(12) United States Patent
Lee et al.

(10) Patent No.: US 6,730,478 B1
(45) Date of Patent: May 4, 2004

(54) METHOD OF MONITORING THE TEMPERATURE OF A BIOCHEMICAL REACTION

(75) Inventors: Martin A Lee, Salisbury (GB); Gale Brightwell, Salisbury (GB)

(73) Assignee: The Secretary of State for Defence in Her Britannic Majesty's Government of the United Kingdom of Great Britain and Northern Ireland, Wiltshire (GB)

(*) Notice: Subject to any disclaimer, the term of this patent is extended or adjusted under 35 U.S.C. 154(b) by 0 days.

(21) Appl. No.: 09/786,521

(22) PCT Filed: Sep. 3, 1999

(86) PCT No.: PCT/GB99/02933

§ 371 (c)(1), (2), (4) Date: Mar. 6, 2001

(87) PCT Pub. No.: WO00/14278

PCT Pub. Date: Mar. 16, 2000

(30) Foreign Application Priority Data

Sep. 7, 1998 (GB) .............................................. 9819417

(51) Int. Cl.⁷ ........................... C12P 19/34; C12Q 1/68; C07H 21/02; C07H 21/04
(52) U.S. Cl. .......................... 435/6; 435/91.2; 536/23.1; 536/24.3
(58) Field of Search ................... 435/6, 91.2; 536/23.1, 536/24.3

(56) References Cited

U.S. PATENT DOCUMENTS 5,607,834 A * 3/1997 Bagwell
5,736,333 A * 4/1998 Livak et al.
5,866,336 A * 2/1999 Nazarenko et al.
5,925,517 A * 7/1999 Tyagi et al.
5,994,056 A * 11/1999 Higuchi

FOREIGN PATENT DOCUMENTS

WO  WO97/46714    12/1997
WO  WO9746714   * 12/1997
WO  WO98/36096    8/1998
WO  WO9836096   *  8/1998

OTHER PUBLICATIONS

Ririe et al., Analytical Biochemistry 245 :156–160 (1997).*
Ederhof et al. J. of Biochemical and Biophysical Methods 37 :99–104 (Nov. 18, 1998).*
Hiyoshi et al. Analytical Biochemistry 221: 306–311 (1994).*
Wittwer C T et al.: "Continuous Fluorescence Monitoring of Rapid Cycle DNA Amplification" Biotechniques, US, Eaton Publishing, Natick, vol. 22, No. 1, Jan. 1997, pp. 130–131.
Lay and Wittwer: "Real–Time Fluorescence Genotyping of Factor v Leiden During Rapid–Cycle PCR" Clin. Chem., vol. 43, No. 12, 1997, pp. 2262–2267.
Bernard et al.: "Integrated Amplification and Detection of the C6771 Point Mutation in the Methylenetetrahydrofolate Reductase Gene by Fluoresecence Resosnance Energy Transfer and Probe Melting Curves" Anal. Biochem., vol. 255, Jan. 1998, pp. 101–107.
Cantor: "Lighting up Hybridization" Nature Biotechnology, US, Nature Publishing, vol. 14, 1996, p. 247.

* cited by examiner

Primary Examiner—Ethan Whisenant
(74) Attorney, Agent, or Firm—Nixon & Vanderhye P.C.

(57) ABSTRACT

A method for monitoring the temperature of a biochemical reaction is disclosed. The method effects the reaction in the presence of a fluorescently labeled DNA probe which comprises a double stranded region which dentures at a predetermined temperature. The fluorescent label is arranged so that a detectable signal is generated upon denaturation of the probe.

7 Claims, 4 Drawing Sheets

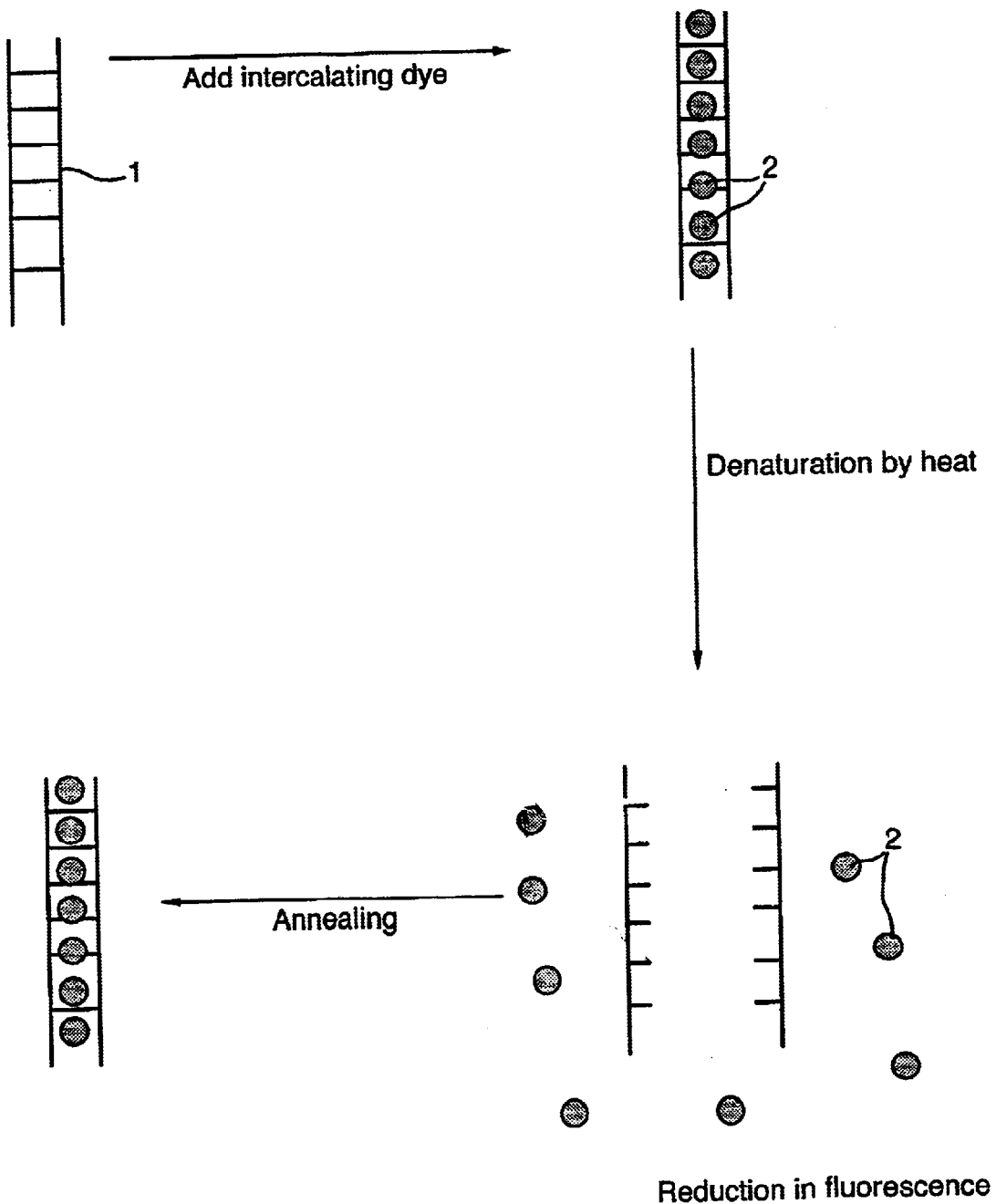

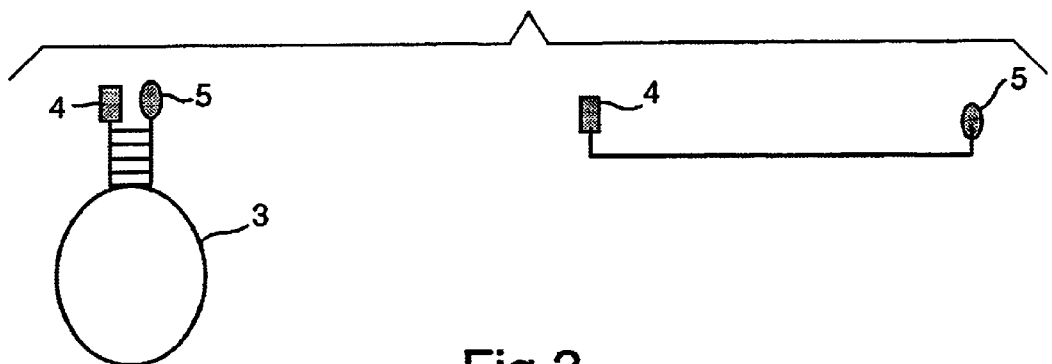
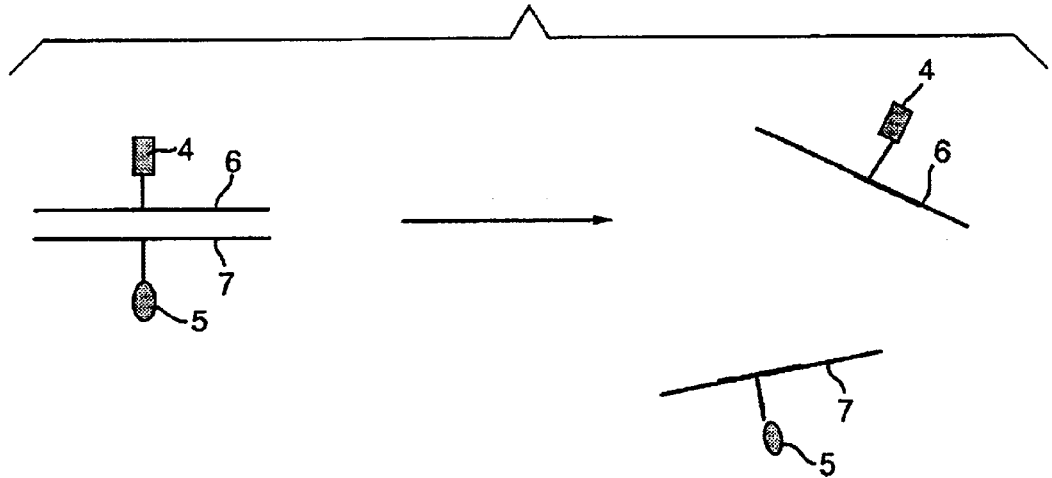
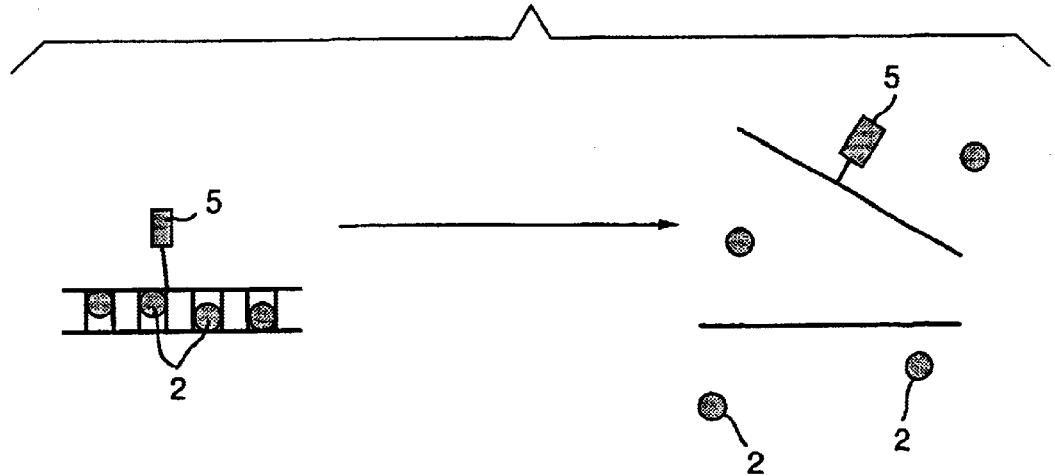

INTERNAL CONTROLS

——————— 20%
40%
50%
60% or
80% GC

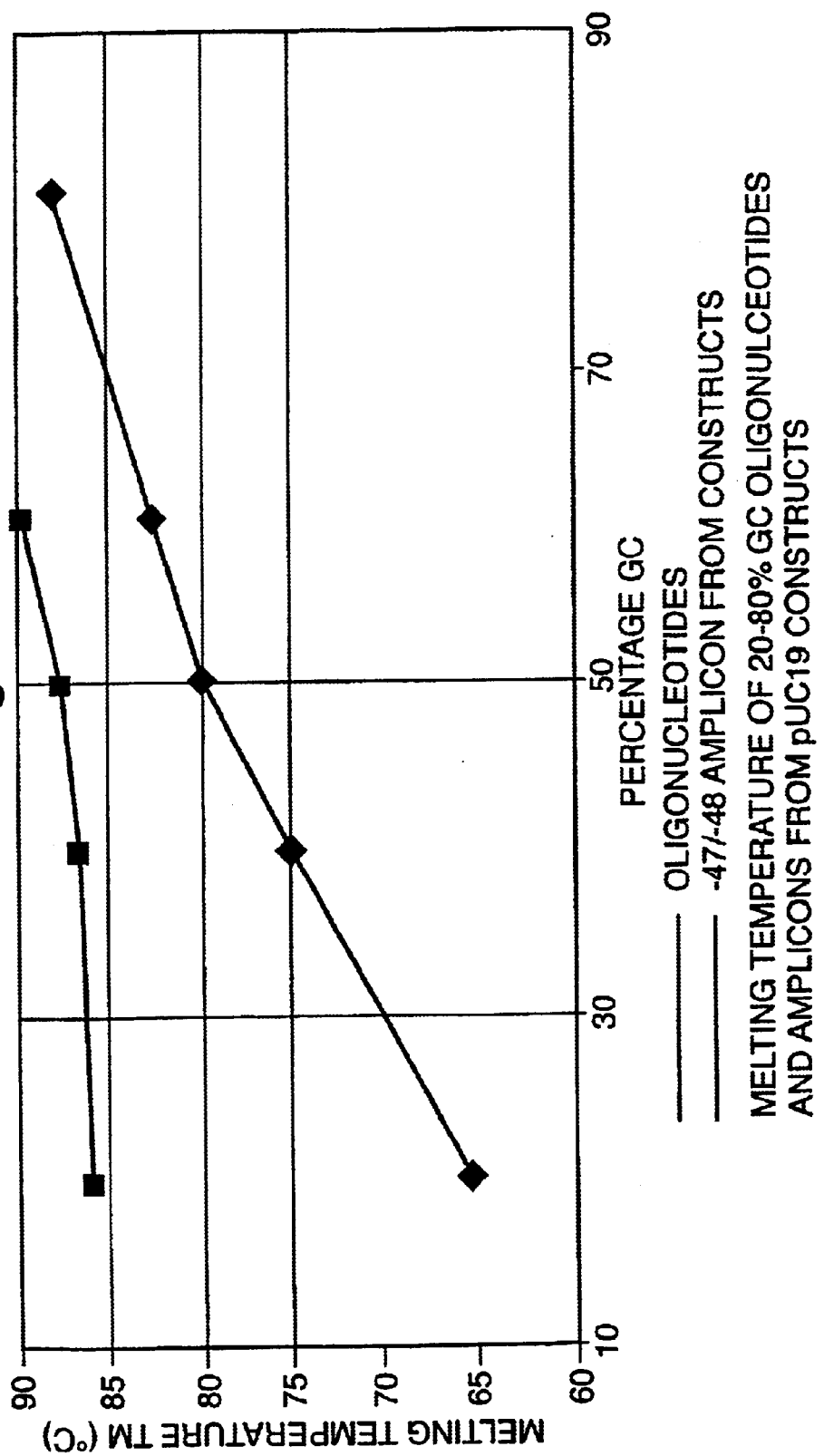

METHOD OF MONITORING THE TEMPERATURE OF A BIOCHEMICAL REACTION

The present invention relates to a method of carrying out an amplification reaction and in particular a polymerase chain reaction (PCR) using an internal temperature control mechanism.

A common problem in biochemical reactions, in particular miniaturised biochemical reactions is controlling the temperature. Invasive temperature probes add to the thermal mass of the sample and increase time constraints associated with heating and cooling. A particular example where such a problem occurs is with minaturised amplification reactions such as the PCR reaction. In this reaction, cycling between various accurate temperatures is an essential element. In outline, the procedure consists of the following steps, repeated cyclically. Denaturation : A mixture containing the PCR reagents (including the DNA to be copied, the individual nucleotide bases (A,T,G,C), suitable primers and polymerase enzyme) are heated to a predetermined temperature to separate the two strands of the target DNA.

Annealing: The mixture is then cooled to another predetermined temperature and the primers locate their complementary sequences on the DNA strands and bind to them.

Extension: The mixture is heated again to a further predetermined temperature. The polymerase enzyme (acting as a catalyst) joins the individual nucleotide bases to the end of the primer to form a new strand of DNA which is complementary to the sequence of the target DNA, the two strands being bound together.

Any interference with the reaching the predetermined temperatures as a result of the temperature measurement can present a significant problem in terms of the success of the amplification reaction.

The applicants have found a way in which the temperature present in a biochemical reaction can be monitored without the need for the application of temperature probes.

According to the present invention there is provided a method of monitoring the temperature of a biochemical reaction, said method comprising effecting the reaction in the presence of a fluorescently labelled temperature probe DNA sequence which comprises a double stranded region which denatures at a predetermined temperature, the fluorescent label or said temperature probe sequence being arranged so that the nature of the fluorescence changes at the point at which denaturation of the said region takes place; and monitoring fluorescence from said reaction mixture so as to determine when the said predetermined temperature has been reached.

The labelled temperature probe DNA sequence added to the reaction mixture in the method acts as a temperature probe allowing the temperature of the reaction to be accurately set without requiring external temperature probes.

The temperature probe DNA sequence may comprise a double stranded DNA sequence, or it may be in the form of a single nucleic acid strand, end regions of which hybridise together so as to form a loop or "hairpin" structure.

Suitable fluorescent labels include intercalating dyes, which are interposed between the strands of a double stranded region of a DNA sequence. When the double stranded DNA region containing the intercalating dye reaches the predetermined temperature, it will be denatured, thus releasing the intercalating dye present between the strands. At this point the fluorescence from the mixture will reduce significantly, giving a readable signal.

BRIEF DESCRIPTION OF THE DRAWINGS

The process using a double stranded DNA sequence as a temperature probe is illustrated diagrammatically in FIG. 1 hereinafter.

When intercalating dye (2) is added to a solution of double stranded DNA (1), it becomes interposed between the strands. The concentration of the dye (2) in this way produces a recognisable signal. On heating of the DNA so that it is denatured, dye is released and this event can be witnessed. Cooling to a temperature at which the said sequence will anneal again results in the intercalating dye becoming again trapped between the strands (see FIG. 1).

Figure 5:
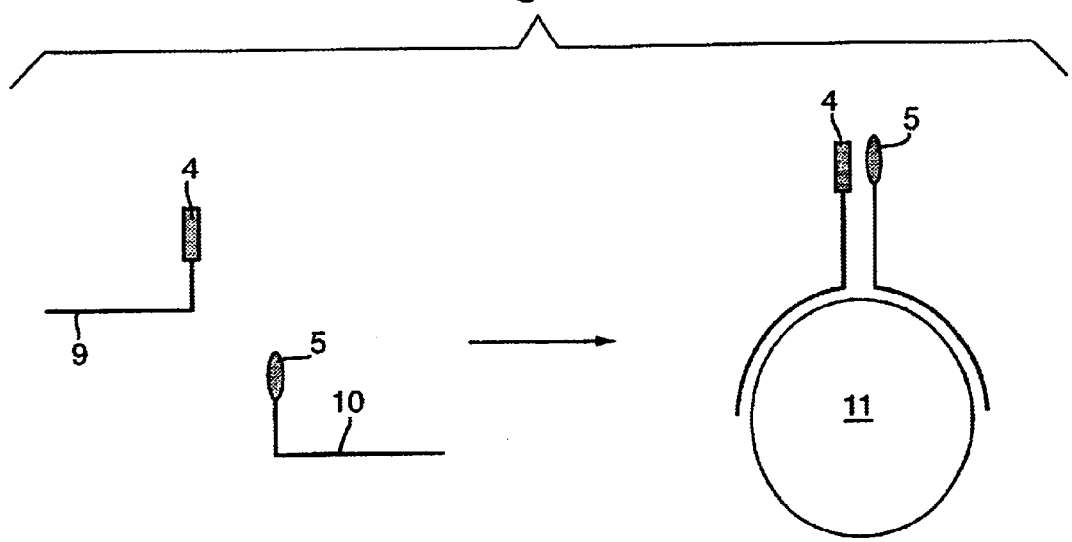

Suitable intercalating dyes include SYBRGreen™, SYBRGold™ and ethidium bromide or other commercially available dyes.

Alternatively, the fluorescent label used in the method of the invention may utilise fluorescence resonance transfer (FRET) as the basis of the signal. These labels utilise the transfer of energy between a reporter and a quencher molecule. The reporter molecule is excited with a specific wavelength of light for which it will normally exhibit a fluorescence emission wavelength. The quencher molecule is also excited at this wavelength such that it can accept the emission energy of the reporter molecule by resonance transfer when they are in close proximity (e.g. on the same, or a neighboring molecule). The basis of FRET detection is to monitor the changes at reporter and quencher emission wavelengths.

For use in the context of the present invention, the DNA sequence used as a temperature probe can be provided with a reporter and a quencher molecule, arranged so that the hybridisation of the strands alters the spatial relationship between the quencher and reporter molecules. Examples of such arrangements are illustrated in FIG. 2 and FIG. 3.

FIG. 2 illustrates an Example where the temperature probe sequence is a single stranded "hairpin" type sequence (3), where the end portions hybridise together. A reporter molecule (4) is attached in the region of either the 5' or the 3' end of the sequence and a quencher molecule (5) is attached at the opposite end such that they are brought into close proximity when the sequence is in the form of the loop. In this arrangement, FRET occurs and so fluorescent signal from the reporter molecule is reduced whilst the signal from the quencher (5) molecule is enhanced.

On denaturation however, the opposed end regions of the sequence separate so that the reporter and quencher molecules become spaced and so FRET no longer occurs. This changes the signals from the respective molecules and so this event can be detected.

Another arrangement is illustrated in FIG. 3. In this case, the reporter (4) and quencher molecules (5) are located on different strands (6,7 respectively) of a DNA temperature probe sequence and are located such that on hybridisation of the strands, they are brought into close proximity to each other so that FRET can occur.

Yet a further embodiment is illustrated in FIG. 4. In this case, an intercalating dye (2) is used as an element of the FRET system. A quencher molecule (5) which can absorb radiation from the dye may be arranged on a strand of the temperature probe sequence such that it can absorb radiation from dye which is close proximity to on hybridisation of the strands. When the temperature probe sequence reaches a temperature at which it is denatured, the dye (2) is dispersed and so the signal from the quencher molecule (5) changes.

This embodiment is advantageous in that only a single label need be applied to the temperature probe sequence. Single labelled sequences of this type are more economical to produce.

In yet a further embodiment (FIG. 5), the reporter (4) and quencher (5) molecules are positioned on two oligonucleotide strands (9 and 10 respectively) which do not hybridise together. They are however designed so that in use, they hydridise to a DNA sequence present in the reaction mixture, which may be a plasmid (11), such that the reporter (4) and quencher (5) are brought into close proximity and FRET can occur between them, giving a recognisable signal.

The DNA sequence to which they bind may be part of the reaction system, for example where the reaction being monitored is a PCR reaction wherein the DNA sequence comprises or is part of the amplification target sequence. Alternatively, the sequences may be added to the reaction in order to provide the basis for the temperature probe of the invention.

The temperature probe sequence of the invention may be designed so that it denatures at any desired predetermined temperature. For example, the denaturation temperature of a sequence depends to some extent on its length. Longer sequences will denature or melt at higher temperatures. Furthermore, it is known that the bases C and G bind together more strongly than A and T. Therefore, the greater the higher the content of the bases G and C contained within a sequence, the higher the melting point of the sequence will be. This feature is illustrated in FIG. 5 which shows the melting temperature of a DNA sequence plotted against the percentage of and GC base pairs which are present within in. Thus, by adjusting the GC content, the temperature probe sequence may be designed so that, if desired, it also has a predetermined length.

The method of the invention is particularly applicable for use in amplification reactions such as the polymerase chain reaction (PCR). In this case, the temperature probe sequence of the invention is introduced into the reaction vessel. Suitably the temperature probe sequence is designed such that it generates a detectable signal when it reaches the optimum annealing temperature of the target DNA sequence as this is intermediate temperature is most difficult to set accurately in practice. However, more than one such temperature probe sequence may be added and arranged to provide appropriate and preferably different signals when the predetermined extension and/or denaturation temperatures have been reached.

Figure 6:
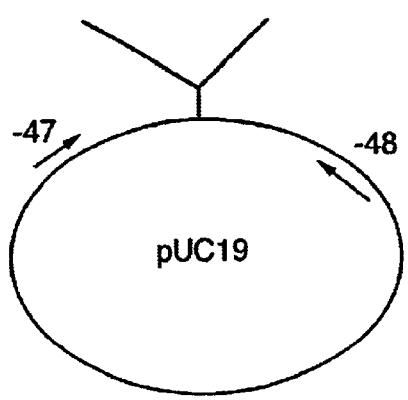

The invention will now be particularly described by way of example with reference to the accompanying diagrammatic drawings in which:

FIG. 1 illustrates the formation and use of a labelled temperature probe sequence for use in the method of the invention;

FIGS. 2 to 5 represent alternative embodiments of the labelled temperature probe sequences of the invention and the denaturation thereof;

FIG. 6 illustrates a construct used in the examples hereinafter; and

FIG. 7 shows the melting temperature of plasmid constructs and inserts as measured using the method of the invention, as a function of the percentage GC content of the construct, where the lighter line represents the oligonucleotides and the darker line represents the −47/−48 amplicon from constructs.

EXAMPLE 1

Oligonucleotides, 60 base pairs in length, were designed by randomly removing the letters G, A, T and C from a paper bag. Complementary pairs of the thus formed random oligonucleotides were mixed together at a final concentration of 1 $\mu$M and 1:40,000 dilution of SYBRGreen™ reference dye. The mixtures were then loaded into LightCycler™ tubes and the temperature slowly raised from 40° C. to 110° C. The fluorescence at 520 nm was measured and was seen to drop off as the temperature was raised. The differential of fluorescence was used to determine the peak rate of change (i.e. drop) which corresponds to the strands melting. 20%, 40%, 50% 60% and 80% GC oligos were used in different experiments. The results, expressed as a graph of melting temperature vs GC content is shown as FIG. 7.

EXAMPLE 2

The different GC duplexes used in Example 1 were cloned into the vector polylinker of pUC19 plasmid as illustrated in FIG. 6. This plasmid was subjected to a polymerase chain reaction using vector primer sites, the −47 and −48 sequencing primer sites. The PCR reaction contained 1:40,000 dilution of SYBRGold™ reference dye. After PCR on the LightCycler™, the products were melted off as described in Example 1. The melting temperature of the different amplicons vs the GC content is shown on the graph (FIG. 7).

What is claimed is:

1. A method of monitoring the temperature of a biochemical reaction in a reaction mixture, said method comprising effecting the reaction in the presence of a fluorescently labelled temperature probe DNA sequence which comprises a double stranded region which denatures at a predetermined temperature, the fluorescent label of said temperature probe sequence being arranged so that a detectable signal occurs at the point at which denaturation of said region takes place; and monitoring fluorescence from said reaction mixture so as to determine when said predetermined temperature has been reached, wherein the temperature probe comprises a single nucleic acid strand, end regions of which hybridise together so as to form a loop or hairpin structure and wherein the fluorescent label comprises an intercalating dye.

2. A method of monitoring the temperature of a biochemical reaction in a reaction mixture, said method comprising effecting the reaction in the presence of a fluorescently labelled temperature probe DNA sequence which comprises a double stranded region which denatures at a predetermined temperature, the fluorescent label of said temperature probe sequence being arranged so that a detectable signal occurs at the point at which denaturation of said region takes place; and monitoring fluorescence from said reaction mixture so as to determine when said predetermined temperature hasp been reached, wherein the fluorescent label utilises fluorescence transfer (FRET) as the basis of the signal and wherein the temperature probe DNA sequence is provided with a reporter and a quencher molecule, the reporter and quencher molecules being located on different strands of a DNA temperature probe sequence, and arranged such that on hybridisation of the strands, they are brought into close proximity to each other.

3. A method according to claim 2 wherein FRET is established between an intercalating dye and a quencher molecule arranged on a strand of the temperature probe sequence such that is can absorb radiation from dye which is in close proximity on hybridisation of the strands.

4. A method of monitoring the temperature of a biochemical reaction in a reaction mixture, said method comprising effecting the reaction in the presence of a fluorescently labelled temperature probe DNA sequence which comprises a double stranded region which denatures at a predetermined temperature, the fluorescent label of said temperature probe sequence being arranged so that a detectable signal occurs at the point at which denaturation of said region takes place; and monitoring fluorescence from said reaction mixture so as to determine when said predetermined temperature has been reached, wherein the fluorescent label utilises fluorescence transfer (FRET) as the basis of the signal and wherein the temperature probe DNA sequence comprises a first DNA strand having a reporter molecule thereon, a second DNA strand having a quencher molecule thereon, said first and second DNA strands being designed to hybridise to a third DNA stand such that the reporter and quencher molecules are brought into close proximity with each other.

5. A method according to claim 1, 2, 3 or 4 wherein the biochemical reaction is an amplification reaction.

6. A method according to claim 5 wherein the amplification reaction is a polymerase chain reaction.

7. A method according to claim 6 wherein the length of the temperature probe is similar to that of an amplicon of the polymerase chain reaction.

* * * * *